United States Patent
Schnorr et al.

(10) Patent No.: US 8,609,386 B2
(45) Date of Patent: Dec. 17, 2013

(54) POLYPEPTIDES HAVING TYROSINASE ACTIVITY AND POLYNUCLEOTIDES ENCODING SAME

(75) Inventors: Kirk Matthew Schnorr, Holte (DK); Jeppe Wegener Tams, Gentofte (DK); Christel Thea Joergensen, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 562 days.

(21) Appl. No.: 12/674,798

(22) PCT Filed: Sep. 16, 2008

(86) PCT No.: PCT/EP2008/062300
§ 371 (c)(1),
(2), (4) Date: Feb. 23, 2010

(87) PCT Pub. No.: WO2009/037253
PCT Pub. Date: Mar. 26, 2009

(65) Prior Publication Data
US 2011/0217414 A1   Sep. 8, 2011

Related U.S. Application Data

(60) Provisional application No. 60/973,600, filed on Sep. 19, 2007.

(30) Foreign Application Priority Data

Sep. 18, 2007   (EP) ..................................... 07116689

(51) Int. Cl.
*C12N 9/02*      (2006.01)
*C12Q 1/26*      (2006.01)
*C07K 14/00*     (2006.01)
*C12P 21/00*     (2006.01)

(52) U.S. Cl.
USPC ............. 435/189; 435/25; 435/69.1; 530/350

(58) Field of Classification Search
USPC ........................... 435/189, 69.1, 25; 530/350
See application file for complete search history.

(56) References Cited

FOREIGN PATENT DOCUMENTS

WO    WO 2006/084953    8/2006

OTHER PUBLICATIONS

Kanda et al., GenBank accession No. BAD51402, 2004.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Guo et al., PNAS 101(25):9205-9210, 2004.*
Kanda et al, Accession No. AB120567, pp. 1-2 (2004).
Selinheimo et al, Journal of Biotechnology, vol. 130 pp. 471-480 (2007).
Selinheimo et al, The FEBS Journal, vol. 273, pp. 4322-4335 (2006).
Wichers et al, Applied Microbiol Biotechnology, vol. 61, pp. 336-341 (2003).
Decker et al, Trends in Biochemistry Science, vol. 25, pp. 392-397 (2000).
International Search Report of PCT/EP2008/062300, pp. 1-7 (mailed May 26, 2009).

* cited by examiner

*Primary Examiner* — Delia Ramirez
(74) *Attorney, Agent, or Firm* — Kristin J. McNamara

(57) ABSTRACT

The present invention relates to isolated polypeptides having tyrosinase activity and isolated polynucleotides encoding the polypeptides. The invention also relates to nucleic acid constructs, vectors, and host cells comprising the polynucleotides as well as methods for producing, activating and using the polypeptides.

17 Claims, No Drawings

SEQUENCE LISTING

<160> NUMBER OF SEQ ID NOS: 9

<210> SEQ ID NO 1
<211> LENGTH: 1641
<212> TYPE: DNA
<213> ORGANISM: Botryosphaeria obtusa

<400> SEQUENCE: 1
atgcgtcttt tcgacatctc tgcggcactc ggtgcccttt gccttttctc tctcggggcc 60
aatgcctctc cgattgagcc tgggctcgtc gagaggcaaa gctccttctt tgctctcact 120
ggcgctggcg gcgggacgtc ccctcgcctg gaagttcgcg acctggcagc caatgcggac 180
caatggaatc tcttccttct tgctatgcaa cgcttccaat ccaaacctca ggccaataag 240
ttgtcgtact accaagttgc cggcattcac ggacgtcctt atgtcaactg ggatggcgtt 300
gcggcgtata catcccagcc gtattggccc ggctactgcc cccacagctc caatctcttc 360
gggacttggc acagacctta catatccctg tttgagcaac tcgttctcca gtacgccaac 420
gagattatca acgaatcccc agctggtgcc accaagacca agtatcagac tgcggtcaaa 480
acgctacgat tcccgttctg ggattgggcc aagaaaacat cttctgtcat cccggggcct 540
ctctcgcagg ctaccgttcg agtcacgttc cctcaaaacg gaacctcgac gagtattccg 600
aaccctgtct acgcctatag gttccaagtt gtaccggacc ccaacttcga cggcagctac 660
gccaataacc gtcagacgct tcgttcgagc agcgctgagg ccaacctcca ggcttcatac 720
accagccgcc gcaacacact tttgacacta ttcagtagga accaggccta caacacgttt 780
agcactgacg cgaacggcaa tactgctccc aacttggagg gcatccacaa cggcgtccat 840
aatgatattg gtggctacat gcagcagatc gcctactctg ctatggatcc tatctttgcc 900
atgcaccatg caaacgtgga taggattgtt gccatctggc agaagcttta ccccaacagc 960
tacgtggctg ccgcgtctca agccgccggc actaggacga tagcgccagg aaccagccgt 1020
gacgccaact ctccgctcac gcccttccac cgagacacgg gcggtacctt ctggacctcg 1080
aacacggtcc gcgacacgac ggttttgggc tacacgtacc cggacttggt gggcgtcagc 1140
aactcacagc tcaccaccaa cctcaatcgc ctgtacggca acactgctac caacacggcg 1200
ctgcgggtca ccggcaccgg ggatacttcg gccaccactt atgactacat ggccatggtc 1260
actctcgaca agagcgtgct gggcggaatg tcgtatgcag tgcgattcct tctgaacggc 1320
cagtacttcg cctccttcgc ggccctggca gttccccagc caccgggtgg gcagacaaag 1380
gcggtgacca gctccggcac ggtcatgctc acggctgcgc tggccgagag aggcgtcgac 1440
acgtccgacc gcgaggccac ggagcagtac ctcagcgaga acctcaagtg gcaggtggtg 1500
cagaacgatc aggttgtcaa caacgtcccc agcctcaacg tcactatcgc cagcactgag 1560
gtcaagccgg ccaaggcgac gaaccagttt gccacatggc tcgggcctcc gcaggaaatt 1620
gacaacagta cttcgtcttc g 1641

<210> SEQ ID NO 2
<211> LENGTH: 547
<212> TYPE: PRT
<213> ORGANISM: Botryosphaeria obtusa

<400> SEQUENCE: 2

Met Arg Leu Phe Asp Ile Ser Ala Ala Leu Gly Ala Leu Cys Leu Phe
1 5 10 15

Ser Leu Gly Ala Asn Ala Ser Pro Ile Glu Pro Gly Leu Val Glu Arg

-continued

```
             20                  25                  30
Gln Ser Ser Phe Phe Ala Leu Thr Gly Ala Gly Gly Thr Ser Pro
             35                  40                  45
Arg Leu Glu Val Arg Asp Leu Ala Ala Asn Ala Asp Gln Trp Asn Leu
 50                  55                  60
Phe Leu Leu Ala Met Gln Arg Phe Gln Ser Lys Pro Gln Ala Asn Lys
 65                  70                  75                  80
Leu Ser Tyr Tyr Gln Val Ala Gly Ile His Gly Arg Pro Tyr Val Asn
                 85                  90                  95
Trp Asp Gly Val Ala Ala Tyr Thr Ser Gln Pro Tyr Trp Pro Gly Tyr
                100                 105                 110
Cys Pro His Ser Ser Asn Leu Phe Gly Thr Trp His Arg Pro Tyr Ile
                115                 120                 125
Ser Leu Phe Glu Gln Leu Val Leu Gln Tyr Ala Asn Glu Ile Ile Asn
                130                 135                 140
Glu Ser Pro Ala Gly Ala Thr Lys Thr Lys Tyr Gln Thr Ala Val Lys
145                 150                 155                 160
Thr Leu Arg Phe Pro Phe Trp Asp Trp Ala Lys Lys Thr Ser Ser Val
                165                 170                 175
Ile Pro Gly Pro Leu Ser Gln Ala Thr Val Arg Val Thr Phe Pro Gln
                180                 185                 190
Asn Gly Thr Ser Thr Ser Ile Pro Asn Pro Val Tyr Ala Tyr Arg Phe
                195                 200                 205
Gln Val Val Pro Asp Pro Asn Phe Asp Gly Ser Tyr Ala Asn Asn Arg
                210                 215                 220
Gln Thr Leu Arg Ser Ser Ala Glu Ala Asn Leu Gln Ala Ser Tyr
225                 230                 235                 240
Thr Ser Arg Arg Asn Thr Leu Leu Thr Leu Phe Ser Arg Asn Gln Ala
                245                 250                 255
Tyr Asn Thr Phe Ser Thr Asp Ala Asn Gly Asn Thr Ala Pro Asn Leu
                260                 265                 270
Glu Gly Ile His Asn Gly Val His Asn Asp Ile Gly Gly Tyr Met Gln
                275                 280                 285
Gln Ile Ala Tyr Ser Ala Met Asp Pro Ile Phe Ala Met His His Ala
                290                 295                 300
Asn Val Asp Arg Ile Val Ala Ile Trp Gln Lys Leu Tyr Pro Asn Ser
305                 310                 315                 320
Tyr Val Ala Ala Ser Gln Ala Ala Gly Thr Arg Thr Ile Ala Pro
                325                 330                 335
Gly Thr Ser Arg Asp Ala Asn Ser Pro Leu Thr Pro Phe His Arg Asp
                340                 345                 350
Thr Gly Gly Thr Phe Trp Thr Ser Asn Thr Val Arg Asp Thr Thr Val
                355                 360                 365
Leu Gly Tyr Thr Tyr Pro Asp Leu Val Gly Val Ser Asn Ser Gln Leu
                370                 375                 380
Thr Thr Asn Leu Asn Arg Leu Tyr Gly Asn Thr Ala Thr Asn Thr Ala
385                 390                 395                 400
Leu Arg Val Thr Gly Thr Gly Asp Thr Ser Ala Thr Thr Tyr Asp Tyr
                405                 410                 415
Met Ala Met Val Thr Leu Asp Lys Ser Val Leu Gly Met Ser Tyr
                420                 425                 430
Ala Val Arg Phe Leu Leu Asn Gly Gln Tyr Phe Ala Ser Phe Ala Ala
                435                 440                 445
```

```
Leu Ala Val Pro Gln Pro Pro Gly Gly Gln Thr Lys Ala Val Thr Ser
        450                 455                 460

Ser Gly Thr Val Met Leu Thr Ala Ala Leu Ala Glu Arg Gly Val Asp
465                 470                 475                 480

Thr Ser Asp Arg Glu Ala Thr Glu Gln Tyr Leu Ser Glu Asn Leu Lys
                485                 490                 495

Trp Gln Val Val Gln Asn Asp Gln Val Val Asn Asn Val Pro Ser Leu
                500                 505                 510

Asn Val Thr Ile Ala Ser Thr Glu Val Lys Pro Ala Lys Ala Thr Asn
        515                 520                 525

Gln Phe Ala Thr Trp Leu Gly Pro Pro Gln Glu Ile Asp Asn Ser Thr
    530                 535                 540

Ser Ser Ser
545

<210> SEQ ID NO 3
<211> LENGTH: 3897
<212> TYPE: DNA
<213> ORGANISM: Artificial sequence
<220> FEATURE:
<223> OTHER INFORMATION: Plasmid pMHas7

<400> SEQUENCE: 3
aattcggcca ttatggccaa gcagtggtat caacgcagag tacgcggggg ctcgctgctg      60
accaggctct gccggctcct tcggcctcgc cgcaggaact tgctactacc agcaccatgc     120
cctaccaata tccagcactg accccggagc agaagaagga gctgtctgac atcgctcacc     180
gcatcgtggc acctggcaag ggcatcctgg ctgcagatga gtccactggg agcattgcca     240
agcggctgca gtccattggc accgagaaca ccgaggagaa ccggcgcttc taccgccagc     300
tgctgctgac agctgacgac cgcgtgaacc cctgcattgg gggtgtcatc ctcttccatg     360
agacactcta ccagaaggcg gatgatgggc gtcccttccc ccaagttatc aaatccaagg     420
gcggtgttgt gggcatcaag gtagacaagg gcgtggtccc cctggcaggg acaaatggcg     480
agactaccac ccaagggttg gatgggctgt ctgagcgctg tgcccagtac aagaaggacg     540
gagctgactt cgccaagtgg cgttgtgtgc tgaagattgg ggaacacacc ccctcagccc     600
tcgccatcat ggaaaatgcc aatgttctgg cccgttatgc cagtatctgc cagcagaatg     660
gcattgtgcc catcgtggag cctgagatcc tccctgatgg ggaccatgac ttgaagcgct     720
gccagtatgt gaccgagaag gtgctggctg ctgtctacaa ggctctgagt gaccaccaca     780
tctacctgga aggcaccttg ctgaagccca acatggtcac cccaggccat gcttgcactc     840
agaagttttc tcatgaggag attgccatgg cgaccgtcac agcgctgcgc cgcacagtgc     900
cccccgctgt cactgggatc accttcctgt ctggaggcca gagtgaggag gaggcgtcca     960
tcaacctcaa tgccattaac aagtgccccc tgctgaagcc ctgggccctg accttctcct    1020
acggccgagc cctgcaggcc tctgcctga aggcctgggg cgggaagaag agaacctga    1080 aggctgcgca ggaggagtat gtcaagcgag ccctggccaa cagccttgcc tgtcaaggaa    1140
agtacactcc gagcggtcag gctggggctg ctgccagcga gtccctcttc gtctctaacc    1200
acgcctatta gcggaggtg ttccaggct gccccaaca ctccaggccc tgccccctcc    1260
cactcttgaa gaggaggccg cctcctcggg gctccaggct ggcttgcccg cgtctttct    1320 tccctcgtga cagtggtgtg tggtgtcgtc tgtgaatgct aagtccatca cccttccgg    1380 cacactgcca aataaacagc tatttaaggg ggaaaaaaaa aaaaaaaaa aaaaaaaaa    1440 gtacatcgtc actctgctca ctggtcaggc cgcctcggcc cagtcgactc tagactcgag    1500
```

```
caagcttatg catgcggccg ctcgacctgc aggcatgcaa gcttggcact ggccgtcgtt    1560
ttacaacgtc gtgactggga aaaccctggc gttacccaac ttaatcgcct tgcagcacat    1620
ccccctttcg ccagctggcg taatagcgaa gaggcccgca ccgatcgccc ttcccaacag    1680
ttgcgcagcc tgaatggcga atggcgcgat aagctagctt cacgctgccg caagcactca    1740
gggcgcaagg gctgctaaag gaagcggaac acgtagaaag ccagtccgca gaaacggtgc    1800
tgaccccgga tgaatgtcag ctactgggct atctggacaa gggaaaacgc aagcgcaaag    1860
agaaagcagg tagcttgcag tgggcttaca tggcgatagc tagactgggc ggttttatgg    1920
acagcaagcg aaccggaatt gccagctggg cgccctctg gtaaggttgg aagccctgc      1980
aaagtaaact ggatggcttt cttgccgcca aggatctgat ggcgcagggg atcaagatct    2040
gatcaagaga caggatgagg atcgtttcgc atgattgaac aagatggatt gcacgcaggt    2100
tctccggccg cttgggtgga gaggctattc ggctatgact gggcacaaca gacaatcggc    2160
tgctctgatg ccgccgtgtt ccggctgtca gcgcaggggc gcccggttct ttttgtcaag    2220
accgacctgt ccggtgccct gaatgaactc caagacgagg cagcgcggct atcgtggctg    2280
gccacgacgg gcgttccttg cgcagctgtg ctcgacgttg tcactgaagc gggaagggac    2340
tggctgctat tgggcgaagt gccggggcag gatctcctgt catctcacct tgctcctgcc    2400
gagaaagtat ccatcatggc tgatgcaatg cggcggctgc atacgcttga tccggctacc    2460
tgcccattcg accaccaagc gaaacatcgc atcgagcgag cacgtactcg gatggaagcc    2520
ggtcttgtcg atcaggatga tctggacgaa gagcatcagg ggctcgcgcc agccgaactg    2580
ttcgccaggc tcaaggcgcg gatgcccgac ggcgaggatc tcgtcgtgac ccatggcgat    2640
gcctgcttgc cgaatatcat ggtggaaaat ggccgctttt ctggattcat cgactgtggc    2700
cggctgggtg tggcggaccg ctatcaggac atagcgttgg ctacccgtga tattgctgaa    2760
gagcttggcg gcgaatgggc tgaccgcttc ctcgtgcttt acggtatcgc cgctcccgat    2820
tcgcagcgca tcgccttcta tcgccttctt gacgagttct tctgagcggg actctggggt    2880
tcgcgatgat aagctgtcaa acatgagaat tacaacttat atcgtatggg gctgacttca    2940
ggtgctacat ttgaagagat aaattgcact gaaatctaga atatttttat ctgattaata    3000
agatgatctt cttgagatcg ttttggtctg cgcgtaatct cttgctctga aaacgaaaaa    3060
accgccttgc agggcggttt ttcgaaggtt ctctgagcta ccaactcttt gaaccgaggt    3120
aactggcttg gaggagcgca gtcaccaaaa cttgtccttt cagtttagcc ttaaccggcg    3180
catgacttca agactaactc ctctaaatca attaccagtg gctgctgcca gtggtgcttt    3240
tgcatgtctt tccggttgg actcaagacg atagttaccg gataaggcgc agcggtcgga    3300
ctgaacgggg ggttcgtgca tacagtccag cttggagcga actgcctacc cggaactgag    3360
tgtcaggcgt ggaatgagac aaacgcggcc ataacagcgg aatgacaccg gtaaaccgaa    3420
aggcaggaac aggagagcgc acgagggagc cgccagggga aacgcctggt atctttatag    3480
tcctgtcggg tttcgccacc actgatttga gcgtcagatt tcgtgatgct tgtcaggggg    3540
gcggagccta tggaaaaacg ctttgccttc ttttcctgcg ttatcccctg attctgtgga    3600
taaccgtatt accgcctttg agtgagctga taccgctcgc cgcagccgaa cgaccgagcg    3660
cagcgagtca gtgagcgagg aagcggaaga gcgcccaata cgcaaaccgc ctctccccgc    3720
gcgttggccg attcattaat gcagctggca cgacaggttt cccgactgga aagcgggcag    3780
tgagcgcaac gcaattaatg tgagttagct cactcattag gcaccccagg ctttacactt    3840
tatgcttccg gctcgtatgt tgtgtggaat tgtgagcgga taacaatttc acacagg       3897
```

```
<210> SEQ ID NO 4
<211> LENGTH: 20
<212> TYPE: DNA
<213> ORGANISM: Artificial sequence
<220> FEATURE:
<223> OTHER INFORMATION: Primer A

<400> SEQUENCE: 4
agcgtttgcg gccgcgatcc                                              20

<210> SEQ ID NO 5
<211> LENGTH: 21
<212> TYPE: DNA
<213> ORGANISM: Artificial sequence
<220> FEATURE:
<223> OTHER INFORMATION: Primer B

<400> SEQUENCE: 5
ttattcggtc gaaaaggatc c                                            21

<210> SEQ ID NO 6
<211> LENGTH: 32
<212> TYPE: DNA
<213> ORGANISM: Artificial sequence
<220> FEATURE:
<223> OTHER INFORMATION: Primer NP1127RI

<400> SEQUENCE: 6
gcggaattca ccatgcgtct tttcgacatc tc                                32

<210> SEQ ID NO 7
<211> LENGTH: 37
<212> TYPE: DNA
<213> ORGANISM: Artificial sequence
<220> FEATURE:
<223> OTHER INFORMATION: Primer NP1127NotI

<400> SEQUENCE: 7
atttgcggcc gcaaacaagc ccatgataca cgaacag                           37

<210> SEQ ID NO 8
<211> LENGTH: 21
<212> TYPE: DNA
<213> ORGANISM: Artificial sequence
<220> FEATURE:
<223> OTHER INFORMATION: Primer PNA2

<400> SEQUENCE: 8
gtttccaact caatttacct c                                            21

<210> SEQ ID NO 9
<211> LENGTH: 21
<212> TYPE: DNA
<213> ORGANISM: Artificial sequence
<220> FEATURE:
<223> OTHER INFORMATION: Primer TAMG

<400> SEQUENCE: 9
ttgccctcat ccccatcctt t                                            21
```

POLYPEPTIDES HAVING TYROSINASE ACTIVITY AND POLYNUCLEOTIDES ENCODING SAME

CROSS-REFERENCE TO RELATED APPLICATIONS

This application is a 35 U.S.C. 371 national application of PCT/EP2008/062300 filed Sep. 16, 2008, which claims priority or the benefit under 35 U.S.C. 119 of European application no. 07116689.6 filed Sep. 18, 2007 and U.S. provisional application no. 60/973,600 filed Sep. 19, 2007, the contents of which are fully incorporated herein by reference.

REFERENCE TO SEQUENCE LISTING

This application contains a Sequence Listing in computer readable form. The computer readable form is incorporated herein by reference.

REFERENCE TO A DEPOSIT OF BIOLOGICAL MATERIAL

The following biological material has been deposited under the terms of the Budapest Treaty with the DSMZ (Deutsche Sammlung von Mikroorganismen and Zellkulturen GmbH) and given the following accession number and is incorporated herein by reference:

| Deposit | Accession Number | Date of Deposit |
|---------|------------------|-----------------|
| E. coli | DSM 19506 | Jul. 06, 2007 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The tyrosinase encoding gene obtainable from the plasmid in above strain was obtained from *Botryosphaeria obtusa* strain CBS719.85 acquired from the Centraalbureau voor Schimmelcultures.

FIELD OF THE INVENTION

The present invention relates to isolated polypeptides having tyrosinase activity and isolated polynucleotides encoding the polypeptides. The invention also relates to nucleic acid constructs, vectors, and host cells comprising the polynucleotides as well as methods for producing, activating and using the polypeptides.

BACKGROUND OF THE INVENTION

Enzymatic protein modification is frequently used, e.g. in food processing. One purpose of such protein modification is improvement of texture of the food material. Texture is not only related to sensory perception, but also to stability, water holding capacity, gelling and emulsifying properties. Enzyme-aided structure engineering, e.g. via protein cross-linking, can therefore be exploited in several food applications, such as in meat, fish, dairy and cereal foods.

Enzymes having tyrosinase activity have previously been shown to be able to cross-link food proteins. Cross-linking may take place via the formation of o-quinones from protein-bound tyrosine. These o-quinones either condense with each other or react with free amino and sulfhydryl groups present in proteins.

Enzymes for industrial applications are preferably extracellular. Extracellular enzymes, such as secreted enzymes, are usually more stable and can more readily be produced in industrial scale by recombinant technology.

Enzymes having tyrosinase activity have previously been reported. See e.g. WO2006084953 disclosing extracellular tyrosinases obtainable from *Trichoderma* spp. and suggesting various uses of such tyrosinases. At least one of the *Trichoderma* spp. tyrosinases disclosed is proteolytically processed at its C-terminus, whereby about ⅓ of the protein is cleaved off. According to literature, fungal tyrosinases are activated in vivo by limited proteolytic cleavage (Decker, H. and Tuczek, F. (2000) *Trends Biochem. Sci.* 25, 392-397).

It is an object of the present invention to provide polypeptides having tyrosinase activity and polynucleotides encoding the polypeptides. Another object of the present invention is to provide naturally secreted polypeptides that are useful in production of various food products, e.g. due to their ability to cross-link food proteins. Yet another object of the present invention is to provide methods for producing polypeptides having tyrosinase activity and methods for providing such polypeptides in their active form.

SUMMARY OF THE INVENTION

The present invention relates to isolated polypeptides having tyrosinase activity selected from the group consisting of:

(a) a polypeptide having an amino acid sequence which has at least 60% identity with (i) SEQ ID NO: 2, or (ii) amino acids 34 to 392 thereof;

(b) a polypeptide which is encoded by a polynucleotide which is at least 60% identical to (i) SEQ ID NO:1, (ii) nucleotides 100 to 1176 thereof, or (iii) the tyrosinase encoding DNA sequence obtainable from the plasmid in *E. coli* DSM 19506;

(c) a polypeptide which is encoded by a nucleotide sequence which hybridizes under at least low stringency conditions with the complementary strand of (i) SEQ ID NO: 1, or (ii) nucleotides 100 to 1176 thereof; and (d) a polypeptide derived from a polypeptide of (a) by substitution, deletion or addition of one or several amino acids.

The present invention also relates to isolated polynucleotides encoding such polypeptides and to nucleic acid constructs, recombinant expression vectors, and recombinant host cells comprising the polynucleotides.

The present invention also relates to methods for producing such polypeptides having tyrosinase activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to methods for producing a polypeptide having tyrosinase activity, comprising:
(a) providing an isolated polypeptide or a composition comprising an isolated polypeptide; and
(b) processing the polypeptide with an exogenous protease;
wherein the processing of the polypeptide with the protease increases the tyrosinase activity of the polypeptide.

The present invention also relates to methods of using such polypeptides, particularly in the production of food products.

Definitions

Tyrosinase activity: A tyrosinase according to the present invention is an enzyme which oxidizes tyrosine side chains in peptides/proteins and thereby possibly promotes crosslinking, e.g. to other peptides/proteins. A tyrosinase according to the invention may catalyze the o-hydroxylation of monophenols (phenol molecules in which the benzene ring contains a single hydroxyl substituent) to o-diphenols (phenol molecules containing two hydroxyl substituents) and further possibly catalyze the oxidation of o-diphenols to produce o-quinones.

For purposes of the present invention, tyrosinase activity may be determined by any method generally known in the art. L-Dopa or tyrosine can be used as a substrate, where after dopachrome formation may be monitored spectrophotometrically, or alternatively substrate consumption may be monitored by following the oxygen consumption. Tyrosinase activity can also be visualized on agar plates by adding an appropriate substrate such as tyrosine, whereby tyrosinase activity results in a dark zone around the colony.

Tyrosinase activity according to the present invention may be determined by incubating the enzyme with tyrosine or other monophenolic/diphenolic substrates in an appropriate buffer at various pH and temperatures e.g. 50 mM MES at pH 6.5 at 37° C. for 30 minutes and oxygen should be present during the reaction. Prosthetic groups can be added, e.g. $CuCl_2$, to ensure optimal enzyme activity. The enzymatic reaction can be stopped by heat treatment, e.g. 95° C., or extreme pH, e.g. below pH 2 or above pH 10, and the denatured state can be fixed by the addition of sodium EDTA (prevents refolding/reactivation). The enzymatic activity can be followed by spectrophotometric measurements at various wavelengths in the UV/Vis spectra, e.g. at 280 nm and 480 nm.

The polypeptides of the present invention may have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the tyrosinase activity of a polypeptide which is encoded by the nucleotide sequence shown as SEQ ID NO: 1, expressed from a strain of *Aspergillus oryzae* and proteolytically processed to a protein of about 45 kDa as determined by SDS-PAGE.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Identity: The relatedness between two amino acid sequences is described by the parameter "identity".

For purposes of the present invention, the alignment of two amino acid sequences is determined by using the Needle program from the EMBOSS package (available on the Internet at emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 34 to 392 of SEQ ID NO: 2 and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence (e.g. the length of SEQ ID NO: 2 is 547 amino acids).

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of SEQ ID NO: 2 or a homologous sequence thereof, wherein the fragment has tyrosinase activity. Preferably, a fragment contains at least 100 amino acid residues, more preferably at least 200 amino acid residues, and most preferably at least 300 amino acid residues.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having tyrosinase activity. Preferably, a subsequence contains at least 300 nucleotides, more preferably at least 500 nucleotides, and most preferably at least 1000 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the amino acids 1 to 547 of SEQ ID NO: 2 as well as genetic manipulation of the DNA encoding that polypeptide. The modification(s) can be substitution(s), deletion(s) and/or insertions(s) of the amino acid(s) as well as replacement(s) of amino acid side chain(s).

Artificial variant: When used herein, the term "artificial variant" means a polypeptide having tyrosinase activity produced by an organism expressing a modified nucleotide sequence of SEQ ID NO: 1. The modified nucleotide sequence is obtained through human intervention by modification of the nucleotide sequence disclosed in SEQ ID NO: 1.

DETAILED DESCRIPTION OF THE INVENTION

Polypeptides Having Tyrosinase Activity

The present inventors have identified a novel polypeptide having tyrosinase activity. The enzyme is derived from the fungus *Botryosphaeria obtusa*, but it is well suited for recombinant expression from other organisms, e.g. *Aspergillus*. The enzyme is extracellular. It has a signal sequence at its N-terminus, which may be cleaved off during secretion. The enzyme may be further processed, e.g. by further cleavage from the C-terminal end. The enzyme may be produced in an immature form of about 60 kDa, as determined by SDS-PAGE, which has low tyrosinase activity. It may afterwards be processed into a smaller protein of about 40-45 kDa, as determined by SDS-PAGE, which has higher enzymatic activity, which may in the following be referred to as the 45 kDa form or the 45 kDa fragment. The molecular weight depends on, e.g., the degree of modifications such as glycosylation. The processed form may be referred to as the mature enzyme.

A polypeptide of the present invention may therefore have an amino acid sequence which has a degree of identity of at least 60% to a fragment of SEQ ID NO: 2, which has tyrosinase activity. Such fragment may be the mature enzyme. Mass spectrometry analysis of the 45 kDa fragment gives a mass of the presumed non-glycosylated form of 40718 Da, which may include unknown covalent modifications. As estimated from N-terminal sequence analysis, the cleavage site at the N-terminus may be after position 22 or after position 33 of SEQ ID NO: 2. If the cleavage site at the N-terminus is after position 22, the cleavage site at the C-terminus may be after position 392 of SEQ ID NO: 2, giving a mass of 40784 Da. If the cleavage site at the N-terminus is after position 33, the cleavage site at the C-terminus may be after position 402 of SEQ ID NO: 2, giving a mass of 40741 Da. A polypeptide of the present invention may therefore comprise an amino acid sequence which has a degree of identity of at least 60% to amino acids 34 to 392 of SEQ ID NO: 2.

In a first aspect, the present invention relates to isolated polypeptides having an amino acid sequence which has a degree of identity to amino acids 34 to 392 of SEQ ID NO: 2 of at least 60%, preferably at least 65%, more preferably at least 70%, more preferably at least 75%, more preferably at least 80%, more preferably at least 85%, even more preferably at least 90%, most preferably at least 95%, and even most preferably at least 97%, which have tyrosinase activity. In a preferred aspect, a polypeptide of the present invention comprises amino acids 34 to 392 of SEQ ID NO: 2 or an allelic variant thereof or a fragment thereof that has tyrosinase activity. In another preferred aspect, a polypeptide of the present invention comprises amino acids 34 to 392 of SEQ ID NO: 2

In a preferred aspect, a polypeptide of the present invention has an amino acid sequence which has a degree of identity to amino acids 23 to 392 of SEQ ID NO: 2 of at least 60%, preferably at least 65%, more preferably at least 70%, more preferably at least 75%, more preferably at least 80%, more preferably at least 85%, even more preferably at least 90%, most preferably at least 95%, and even most preferably at least 97%. In a more preferred aspect, a polypeptide of the present invention comprises amino acids 23 to 392 of SEQ ID NO: 2 or an allelic variant thereof or a fragment thereof that has tyrosinase activity. In another more preferred aspect, a polypeptide of the present invention comprises amino acids 23 to 392 of SEQ ID NO: 2. In an even more preferred aspect, a polypeptide of the present invention consists of amino acids 23 to 392 of SEQ ID NO: 2 or an allelic variant thereof or a fragment thereof that has tyrosinase activity. In another even more preferred aspect, a polypeptide of the present invention consists of amino acids 23 to 392 of SEQ ID NO: 2.

In a preferred aspect, a polypeptide of the present invention has an amino acid sequence which has a degree of identity to amino acids 34 to 402 of SEQ ID NO: 2 of at least 60%, preferably at least 65%, more preferably at least 70%, more preferably at least 75%, more preferably at least 80%, more preferably at least 85%, even more preferably at least 90%, most preferably at least 95%, and even most preferably at least 97%. In a more preferred aspect, a polypeptide of the present invention comprises amino acids 34 to 402 of SEQ ID NO: 2 or an allelic variant thereof or a fragment thereof that has tyrosinase activity. In another more preferred aspect, a polypeptide of the present invention comprises amino acids 34 to 402 of SEQ ID NO: 2. In an even more preferred aspect, a polypeptide of the present invention consists of amino acids 34 to 402 of SEQ ID NO: 2 or an allelic variant thereof or a fragment thereof that has tyrosinase activity. In another even more preferred aspect, a polypeptide of the present invention consists of amino acids 34 to 402 of SEQ ID NO: 2.

In a preferred aspect, a polypeptide of the present invention has an amino acid sequence which has a degree of identity to SEQ ID NO: 2 of at least 60%, preferably at least 65%, more preferably at least 70%, more preferably at least 75%, more preferably at least 80%, more preferably at least 85%, even more preferably at least 90%, most preferably at least 95%, and even most preferably at least 97%. In a more preferred aspect, a polypeptide of the present invention comprises the amino acid sequence of SEQ ID NO: 2 or an allelic variant thereof or a fragment thereof that has tyrosinase activity. In another more preferred aspect, a polypeptide of the present invention comprises the amino acid sequence of SEQ ID NO: 2. In an even more preferred aspect, a polypeptide of the present invention consists of the amino acid sequence of SEQ ID NO: 2 or an allelic variant thereof or a fragment thereof that has tyrosinase activity. In another even more preferred aspect, a polypeptide of the present invention consists of the amino acid sequence of SEQ ID NO: 2.

In a preferred aspect, a polypeptide of the present invention has an amino acid sequence which differs by ten amino acids, preferably by five amino acids, more preferably by four amino acids, even more preferably by three amino acids, most preferably by two amino acids, and even most preferably by one amino acid from the amino acid sequence of SEQ ID NO: 2. In another preferred aspect, a polypeptide of the present invention has an amino acid sequence which differs by ten amino acids, preferably by five amino acids, more preferably by four amino acids, even more preferably by three amino acids, most preferably by two amino acids, and even most preferably by one amino acid from amino acids 34 to 392 of SEQ ID NO: 2. In another preferred aspect, a polypeptide of the present invention has an amino acid sequence which differs by ten amino acids, preferably by five amino acids, more preferably by four amino acids, even more preferably by three amino acids, most preferably by two amino acids, and even most preferably by one amino acid from amino acids 23 to 392 of SEQ ID NO: 2. In another preferred aspect, a polypeptide of the present invention has an amino acid sequence which differs by ten amino acids, preferably by five amino acids, more preferably by four amino acids, even more preferably by three amino acids, most preferably by two amino acids, and even most preferably by one amino acid from amino acids 34 to 402 of SEQ ID NO: 2.

In another preferred aspect, a polypeptide of the present invention may be (a) a polypeptide whose amino acid sequence comprises amino acids 34 to 392 of the amino acid sequence represented by SEQ ID NO: 2, or (b) a polypeptide derived from (a) by substitution, deletion or addition of one or several amino acids in the amino acid sequence of (a) and having tyrosinase activity. In a more preferred aspect, a polypeptide of the present invention may be (a) a polypeptide whose amino acid sequence is represented by amino acids 23 to 392 of SEQ ID NO: 2, or (b) a polypeptide derived from (a) by substitution, deletion or addition of one or several amino acids in the amino acid sequence of (a) and having tyrosinase activity. In another more preferred aspect, a polypeptide of the present invention may be (a) a polypeptide whose amino acid sequence is represented by amino acids 34 to 402 of SEQ ID NO: 2, or (b) a polypeptide derived from (a) by substitution, deletion or addition of one or several amino acids in the amino acid sequence of (a) and having tyrosinase activity.

In a second aspect, the present invention relates to isolated polypeptides having tyrosinase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 100 to 1176 of SEQ ID NO: 1, (ii) the cDNA sequence contained in nucleotides 100 to 1176 of SEQ ID NO: 1, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of SEQ ID NO: 1 preferably contains at least 100 contiguous nucleotides or more preferably at least 200 contiguous nucleotides. Moreover, the subsequence may encode a polypeptide fragment which has tyrosinase activity.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having tyrosinase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA which hybridizes with the probes described above and which encodes a polypeptide having tyrosinase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 1, its complementary strand, or a subsequence thereof, under very low to very high stringency conditions. Molecules to which the nucleic acid probe hybridizes under these conditions can be detected using X-ray film.

In a preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the mature polypeptide coding region of SEQ ID NO: 1. In another preferred aspect, the nucleic acid probe is the tyrosinase encoding sequence of the plasmid contained in *Escherichia coli* DSM 19506. In another preferred aspect, the nucleic acid probe is the mature tyrosinase coding region of the plasmid contained in *Escherichia coli* DSM 19506.

For long probes of at least 100 nucleotides in length, very low to very high stringency conditions are defined as prehybridization and hybridization at 42° C. in 5× SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[Na^+]) + 0.41(\% \, G+C) - 0.72(\% \text{ formamide})$$

(available on the internet at ndsu.nodak.edu/instruct/mcclean/plsc731/dna/dna6.htm)

Another relevant relationship is that a 1% mismatch of two DNAs lowers the $T_m$ by 1.4° C. To determine the degree of identity required for two DNAs to hybridize under medium stringency conditions at 42° C., the following formula is used:

$$\% \text{ Homology} = 100 - [(\text{Effective } T_m - \text{Hybridization Temperature})/1.4]$$

(available on the internet at ndsu.nodak.edu/instruct/mcclean/plsc731/dna/dna6.htm)

In a third aspect, the present invention relates to an isolated polypeptide which is encoded by a polynucleotide which is at least 60% identical to (i) SEQ ID NO:1, (ii) nucleotides 100 to 1176 thereof, or (iii) the tyrosinase encoding DNA sequence obtainable from the plasmid in *E. coli* DSM 19506. Preferably, the isolated polypeptide is encoded by a polynucleotide which is at least 65%, such as at least 70%, at least 75%, at least 80%, at least 90%, at least 95% or at least 98%, identical to (i) SEQ ID NO:1, (ii) nucleotides 100 to 1176 thereof, or (iii) the tyrosinase encoding DNA sequence obtainable from the plasmid in *E. coli* DSM 19506. Most preferably, the isolated polypeptides having tyrosinase activity are encoded by a polynucleotide comprising nucleotides 100 to 1176 of SEQ ID NO: 1.

In a fourth aspect, the present invention relates to artificial variants comprising a conservative substitution, deletion, and/or insertion of one or more amino acids of SEQ ID NO: 2 or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., tyrosinase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 34 to 392 of SEQ ID NO: 2 is 10, preferably 9, more preferably 8, more preferably 7, more preferably at most 6, more preferably at most 5, more preferably 4, even more preferably 3, most preferably 2, and even most preferably 1.

A polypeptide of the present invention may be active from about pH 4 to about pH 8 and may have a pH optimum at about pH 6 and a temperature optimum at about 50° C. as determined in Example 2 of the present application. Preferably, a polypeptide of the present invention has a pH optimum below pH 8 when measured in a buffer containing 1 mM tyrosine, 100 mM succinic acid, 100 mM HEPES, 100 mM CHES and 1 mM $CuCl_2$ after incubation for 15 min at 25° C., more preferably a pH optimum of between pH 5 and pH 8, and even more preferably a pH optimum of between pH 5 and pH 7.

Sources of Polypeptides Having Tyrosinase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a fungal polypeptide, and more preferably a yeast polypeptide such as a *Candida*, *Kluyveromyces*, *Pichia*, *Saccharomyces*, *Schizosaccharomyces*, or *Yarrowia* polypeptide; or more preferably a filamentous fungal polypeptide such as an *Acremonium, Aspergillus, Aureobasidium, Cryptococcus, Filobasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having tyrosinase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma* koningii, Trichoderma longibrachiatum, Trichoderma reesei, or Trichoderma viride polypeptide.

In a more preferred aspect, the polypeptide is an Ascomycota, such as from the family Botryosphaeriaceae, most preferably from the genus Botryosphaeria, such as, e.g., any of the species B. abietina, B. abrupta, B. abuensis, B. acaciae, B. acutior, B. agaves, B. alibagensis, B. anceps, B. apocyni, B. appendiculata, B. araliae, B. archontophoenicis, B. arctostaphyli, B. arundinariae, B. arxii, B. astrocaryi, B. aterrima, B. australis, B. bakeri, B. bondarzewii, B. brunneispora, B. buteae, B. callicarpae, B. calycanthi, B. camarae, B. carpini, B. cassiicola, B. catervaria, B. cerasi, B. chnaumatica, B. cocogena, B. cocoicola, B. coffeae, B. collematoides, B. corni, B. corticis, B. corticola, B. corynocarpi, B. costai, B. crataegi, B. cruenta, B. cunninghamiae, B. delilei, B. diapensiae, B. diplodioides, B. dispersa, B. dothidea, B. egenula, B. elaeidis, B. epichloe, B. erythrinae, B. escharoides, B. eschweilerae, B. eucalypticola, B. eucalyptorum, B. euphorbii, B. faginea, B. festucae, B. ficus, B. foliicola, B. fuliginosa, B. funtumiae, B. galegae, B. gaubae, B. gleditschiae, B. graphidea, B. halimodendri, B. hamamelidis, B. hemidesmi, B. hibisci, B. horizontalis, B. hyperborea, B. hypericorum, B. hypoxyloidea, B. hysterioides, B. iberica, B. imperspicua, B. indica, B. inflata, B. ingae, B. jasmini, B. juglandina, B. juglandis, B. kumaonensis, B. lanaris, B. laricina, B. laricis, B. liriodendri, B. lutea, B. macrolopha, B. majuscula, B. mall, B. mamane, B. marconii, B. mascarensis, B. melachroa, B. melanommoides, B. melathroa, B. meliae, B. melioloides, B. microspora, B. minor, B. minuscula, B. molluginis, B. mucosa, B. muriculata, B. mutila, B. nephrodii, B. nerii, B. oblongula, B. obtusa, B. pachyspora, B. parkinsoniae, B. parva, B. pasaniae, B. pedrosensis, B. persimon, B. phormii, B. phyllachoroidea, B. piceae, B. pinicola, B. pipturi, B. pittospori, B. plicatula, B. polita, B. polycocca, B. populi, B. prosopidis, B. prospidis, B. protearum, B. pruni, B. prunicola, B. pruni-spinosae, B. pseudotsugae, B. purandharensis, B. pustulata, B. pyriospora, B. quercuum, B. reticulata, B. rhizogena, B. rhodina, B. rhododendri, B. ribis, B. sarmentorum, B. senegalensis, B. simplex, B. smilacinina, B. sorosia, B. spiraeae, B. stevensii, B. stomatica, B. subconnata, B. subglobosa, B. syconophila, B. syringae, B. tamaricis, B. theicola, B. tiampeana, B. tiliacea, B. tjampeana, B. tsugae, B. uleana, B. ulmicola, B. uncariae, B. vanillae, B. vanvleckii, B. venenata, B. vibumi, B. visci, B. viticola, B. vitis, B. wisteriae, B. xanthocephala, B. xanthorrhoeae, B. yedoensis, or B. zeae.

In a most preferred aspect, the polypeptide is a Botryosphaeria obtusa polypeptide, and most preferably a Botryosphaeria obtusa polypeptide obtainable from the plasmid of E. coli DSM 19506, e.g., the polypeptide of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides encoding polypeptides having tyrosinase activity, selected from the group consisting of:

(a) a polynucleotide encoding a polypeptide having an amino acid sequence which has at least 60% identity with i) SEQ ID NO: 2, or (ii) amino acids 34 to 392 thereof;

(b) a polynucleotide having at least 60% identity with (i) SEQ ID NO:1, (ii) nucleotides 100 to 1176 thereof, or (iii) the tyrosinase encoding DNA sequence obtainable from the plasmid in *E. coli* DSM 19506; and (c) a polynucleotide which hybridizes under at least low stringency conditions with the complementary strand of nucleotides 100 to 1176 of SEQ ID NO: 1; and In a preferred aspect, the nucleotide sequence is set forth in SEQ ID NO: 1. In another preferred aspect, the nucleotide sequence is the tyrosinase encoding sequence of the plasmid contained in *Escherichia coli* DSM 19506. In another preferred aspect, the nucleotide sequence is the mature polypeptide coding region of SEQ ID NO: 1. In another preferred aspect, the nucleotide sequence is the mature polypeptide coding region contained in the plasmid of *Escherichia coli* DSM 19506. The present invention also encompasses nucleotide sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have tyrosinase activity.

The present invention also relates to mutant polynucleotides comprising at least one mutation in the mature polypeptide coding sequence of SEQ ID NO: 1, in which the mutant nucleotide sequence encodes a polypeptide comprising amino acids 34 to 392 of SEQ ID NO: 2. In a preferred aspect, the mutant nucleotide sequence encodes a polypeptide comprising amino acids 23 to 392 of SEQ ID NO: 2. In another preferred aspect, the mutant nucleotide sequence encodes a polypeptide comprising amino acids 34 to 402 of SEQ ID NO: 2. In a more preferred aspect, the mutant nucleotide sequence encodes a polypeptide consisting of amino acids 23 to 392 of SEQ ID NO: 2. In another more preferred aspect, the mutant nucleotide sequence encodes a polypeptide which consists of amino acids 34 to 402 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Botryosphaeria*, or another related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 or a fragment thereof, e.g., a sequence comprising nucleotides 100 to 1176, of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode a polypeptide having tyrosinase activity.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for tyrosinase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 100 to 1176 of SEQ ID NO: 1, (ii) the cDNA sequence contained in nucleotides 100 to 1176 of SEQ ID NO: 1, or (iii) a complementary strand of (i) or (ii); or allelic variants and subsequences thereof (Sambrook et al., 1989, supra), as defined herein.

The present invention also relates to isolated polynucleotides obtained or obtainable by (a) hybridizing a population of DNA under very low, low, medium, medium-high, high, or very high stringency conditions with (i) nucleotides 100 to 1176 of SEQ ID NO: 1, (ii) the cDNA sequence contained in nucleotides 100 to 1176 of SEQ ID NO: 1, or (iii) a complementary strand of (i) or (ii); and (b) isolating the hybridizing polynucleotide, which encodes a polypeptide having tyrosinase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for

*Aspergillus niger* neutral alpha-amylase and *Aspergillus oryzae* triose phosphate isomerase); and mutant, truncated, and hybrid promoters thereof.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus orywe* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter; and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota*, and *Zygomycota* (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris,*

*Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Botryosphaeria*, and more preferably *Botryosphaeria obtusa*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the polypeptide coding region of SEQ ID NO: 1, where the mutant nucleotide sequence encodes a polypeptide comprising amino acids 34 to 392 of SEQ ID NO: 2; and (b) recovering the polypeptide. In a preferred embodiment, the mutation in the polypeptide coding sequence of SEQ ID NO: 1 results in the polypeptide encoded having an improved cleavage site for a protease, such as a specific protease.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Methods of Activation

The present invention also relates to methods of producing a polypeptide having tyrosinase activity, comprising (a) providing an isolated polypeptide or a composition comprising an isolated polypeptide; and (b) processing the polypeptide with a protease; wherein the processing of the polypeptide with the protease increases the tyrosinase activity of the polypeptide. Preferably, the polypeptide is a secreted polypeptide.

In a preferred aspect, processing of the polypeptide with the protease comprises cleaving-off of the C-terminal part of the polypeptide. The C-terminal part of the polypeptide may consist of, e.g., at least 10, at least 50, at least 100, at least 200, at least 300 or at least 400 amino acids. In this aspect, cleaving-off of the C-terminal part of the polypeptide increases the tyrosinase activity of the polypeptide, meaning that the unprocessed polypeptide comprising the C-terminal part has less tyrosinase activity than the proteolytically processed polypeptide without the C-terminal part.

The protease may be any suitable protease. Preferably, it is a protease which is exogenous to the cells expressing the tyrosinase. In the context of the present invention, an 'exogenous' enzyme means an enzyme which is produced or originating outside of an organism or a specific cell or cell line. I.e., the protease may be produced by another organism, e.g., another microorganism. The protease may be a protease present in a protein-containing material to be treated with the tyrosinase. In one embodiment of the invention, the protease is a protease naturally occurring in milk, e.g., plasmin. The protease may also be a protease which is added to the enzyme preparation prior to or during its industrial use.

In one embodiment of the invention, the protease is a specific protease and the isolated polypeptide prior to processing comprises a cleavage site for the protease. The cleavage site for the specific protease may be introduced after the amino acid sequence encoding the mature enzyme. Such specific protease may be a protease which has little activity on the proteins naturally occurring in protein containing material to be treated with the tyrosinase. The specific protease may be selected among thrombin, Factor Xa protease or 3C protease from human rhinovirus.

A specific protease in the context of the present invention may mean a protease having specificity for a cleavage site comprising a specific recognition sequence for the protease, and where the protease cleaves with some activity either within the recognition sequence, before the recognition sequence or after the recognition sequence. A cleavage site for a specific protease in the context of the present invention may be any amino acid sequence which is recognised by the protease and triggers it to cut. Preferentially, the cleavage site for a specific protease comprises a recognition sequence which triggers the protease to cut with high activity. The recognition sequence for a specific protease may consist of at least one amino acid. For instance, trypsin specifically cuts after Arg or Lys, unless followed by Pro, and therefore trypsin is a specific protease having specificity for cleavage sites comprising an Arg or a Lys residue, which is not followed by a Pro residue.

Preferentially, in the method of the present invention, a recognition sequence of a cleavage site for a specific protease consists of more than one amino acid. For instance, the specific protease thrombin recognises the consensus sequence Leu-Val-Pro-Arg-Gly-Ser, cleaving the peptide bond between Arg and Gly with high activity. The consensus sequence for a specific protease is the optimal recognition sequence for that protease. Thus, a cleavage site according to the present invention does not necessarily comprise all of the consensus sequence. For thrombin, it is especially the sequence Pro-Arg which is important for recognition, and a cleavage site for thrombin may, e.g., be a sequence triggering thrombin to cleave which comprises Pro-Arg surrounded by any amino acids on both sides.

Factor Xa protease specifically cleaves following the tetrapeptide Ile-Glu-Gly-Arg. It is especially the sequence Gly-Arg which is important for recognition, and a cleavage site for Factor Xa protease may, e.g., be a sequence triggering Factor Xa to cleave which comprises Gly-Arg. (See, e.g., Nagai, K. and Thogersen, H. C. (1984) *Nature* 309, 810, or Nagai, K. and Thøgersen, H. C. (1987) *Methods Enzymol.* 153, 461).

3C protease from human rhinovirus cleaves with high activity between the Gln and Gly residues of the consensus recognition sequence Leu-Glu-Val-Leu-Phe-Gln-/Gly-Pro. A cleavage site for 3C protease from human rhinovirus may, e.g., be a sequence triggering the protease to cleave which comprises some of the amino acids of the consensus sequence. (See, e.g., Cordingley, M. G. et al. (1990) *J. Biol. Chem.* 265, 9062).

The protease, such as the specific protease, may be added to the tyrosinase after its preparation, such as before or during its use in industrial treatment of protein containing material.

The present invention also relates to methods for producing a polynucleotide having a mutant nucleotide sequence, comprising (a) introducing at least one mutation into the polypeptide coding sequence of SEQ ID NO: 1, wherein the mutant nucleotide sequence encodes a polypeptide comprising amino acids 34 to 392 of SEQ ID NO: 2; and (b) recovering the polynucleotide comprising the mutant nucleotide sequence.

Preferably, in such method, the mutation in the polypeptide coding sequence of SEQ ID NO: 1 results in the polypeptide encoded having an improved cleavage site for a protease, e.g. a specific protease, such as a protease selected among thrombin, Factor Xa protease or 3C protease from human rhinovirus.

The present invention also relates to mutant polynucleotide sequences having at least one mutation introduced into the polypeptide coding sequence which results in an improved cleavage site for a protease, wherein the mutant polynucleotide sequence encodes a polypeptide comprising amino acids 34 to 392 of SEQ ID NO: 2.

The present invention also relates to a method for producing a polypeptide comprising amino acids 34 to 392 of SEQ ID NO: 2, said method comprising (a) cultivating a cell comprising a mutant polynucleotide encoding the polypeptide, said polynucleotide having at least one mutation introduced into the polypeptide coding sequence which results in an improved cleavage site for a protease, said cultivation taking place under conditions conducive for production of the polypeptide; and (b) recovering the polypeptide.

Stabilized Tyrosinase Variants

A polypeptide having tyrosinase activity is able to oxidize its own tyrosine residues which are accessible on the surface. These oxidized tyrosines (e.g. quinones) can make covalent crosslinks to other substance which can influence the activity of the polypeptide, e.g. if cross linked to another protein. Such auto-modification of a polypeptide having tyrosinase activity (caused by its own enzymatic activity) can also be made by tyrosinase oxidation of phenolic substances present in the solution. Such oxidized phenolic substances may react with surface accessible amino acid on the tyrosinase, e.g. solvent accessible lysine residues.

Thus especially Tyr and Lys, but also Cys, on the surface of a polypeptide having tyrosinase activity may be changed by site-directed mutagenesis. E.g., Tyr may be replaced with Ala, Cys, Asp, Glu, Phe, Gly, His, Ile, Lys, Leu, Met, Asn, Pro, Gln, Arg, Ser, Thr, Val, Trp; and Lys or Cys could be replace with Ala, Asp, Glu, Phe, Gly, His, Ile, Leu, Met, Asn, Pro, Gln, Arg, Ser, Thr, Val, Trp.

The tyrosinase from *Botryosphaeria obtusa* has 26 Tyr, 13 Lys and 2 Cys and the solvent accessible fraction of these amino acid are potential target for site-directed mutagenesis.

The present invention therefore also relates to a method for preparing a polypeptide comprising:
(a) providing an amino acid sequence of a parent polypeptide having tyrosinase activity;
(b) modifying the sequence by substituting or deleting at least one tyrosine, lysine or cysteine residue;
(c) producing a variant polypeptide having the modified sequence;
(d) testing the variant polypeptide for tyrosinase activity; and
(e) selecting a variant polypeptide having tyrosinase activity.

Preferably, the sequence is modified by substituting or deleting at least one tyrosine residue.

In a preferred aspect, the tyrosine, lysine or cysteine residue to be modified is solvent accessible in the three-dimensional structure of the parent polypeptide.

In another preferred aspect, the amino acid sequence of the parent polypeptide has at least 50% identity, preferably at least 60% or 70% identity, more preferably at least 80%, 90%, 95% or 98% identity, to SEQ ID NO: 2 or amino acids 34 to 392 thereof.

In another preferred aspect, the amino acid sequence of the parent polypeptide comprises (a) amino acids 34 to 392 of SEQ ID NO: 2, or (b) an amino acid sequence having at least 50% identity, preferably at least 60% or 70% identity, more preferably at least 80%, 90%, 95% or 98% identity, to amino acids 34 to 392 of SEQ ID NO: 2.

The present invention also relates to a polypeptide having tyrosinase activity, having an amino acid sequence which:
(a) has at least 50% identity to amino acids 34 to 392 of SEQ ID NO: 2; and
(b) comprises a different amino acid compared to SEQ ID NO: 2 in at least one of the positions where the amino acid of SEQ ID NO: 2 is tyrosine, lysine or cysteine.

Preferably, the amino acid sequence of such polypeptide has at least 60% or 70% identity, more preferably at least 80%, 90%, 95% or 98% identity, to amino acids 34 to 392 of SEQ ID NO: 2.

Preferably, such polypeptide comprises a different amino acid compared to SEQ ID NO: 2 in at least one of the positions where the amino acid of SEQ ID NO: 2 is tyrosine. More preferably, such polypeptide comprises a different amino acid compared to SEQ ID NO: 2 in at least one of the positions where the amino acid of SEQ ID NO: 2 is a tyrosine which is solvent accessible when a polypeptide having the amino acid sequence of SEQ ID NO: 2 is folded into its three-dimensional structure.

Compositions

The present invention also relates to compositions comprising a polypeptide of the present invention. Preferably, the compositions are enriched in such a polypeptide. The term "enriched" indicates that the tyrosinase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deamidase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa;* or *Trichoderma*, preferably *Trichoderma harzianum, Trichoderma koningii, Trichoderma longibrachiatum, Trichoderma reesei,* or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having tyrosinase activity.

The tyrosinases of the present invention are useful in formation of quinones to any kind of matrixes comprising phenolic groups reactive therewith with sub-sequent formation of cross-linking as for example in protein matrices.

The tyrosinases of the present invention may be used for treating any protein containing material, and especially proteins that have a relatively high overall-content or relatively high content of accessible tyrosine residues. Also tyrosine-containing peptides can be modified. The enzymes may be applied in different types of industrial applications, such as in the pharmaceutical, cosmetic, pulp and paper, detergent, and textile industry, and in the feed and food industry.

The tyrosinases of the present invention are especially suitable for treating protein-containing material, wherein the treatment comprises cross-linking of tyrosine-containing proteins.

The tyrosinases of the present invention are especially suitable for treating protein-containing food, particularly meat, dairy, vegetable and cereal materials.

By cross-linking food proteins with the tyrosinase the texture and rheological properties of the food product can be improved.

Treatment of e.g. fish, poultry or other meat products with the polypeptides of the present invention may be useful for obtaining a product with good texture using decreased quantities of other structure forming agents. The polypeptides may also be used for gelling, whereby the use of gelatin can be avoided. The polypeptides may further be used for preventing syneresis i.e. separation of the water phase, which is a problem in a number of milk products, especially if the fat content is low. For example in preparing yoghurt, and especially low calorie yoghurt, the solid and the liquid phase tend to separate during storage. This is disapproved by the consumer, and can be prevented by treating the raw materials in yoghurt with a polypeptide according to the present invention. The polypeptides may also be applied in bakery processes e.g. for hardening the dough, which is especially desired in making frozen dough products.

The polypeptides may further be used for producing L-Dopa, which is useful in the treatment of Parkinson's disease, and in the production of melanins, which are ingredients for the cosmetic industry. In addition, the polypeptides may be used for cross-linking proteinaceous fibres or fibre-derived polymers, such as silk, wool, cashmere, alpaca, or human hair.

The present invention is further described by the following examples which should not be construed as limiting the scope of the invention.

EXAMPLES

Chemicals used as buffers and substrates were commercial products of at least reagent grade.

In the following, ug means micrograms and ul means microliter.

Example 1

Cloning and Expression of Tyrosinase from *Botryosphaeria obtusa* cDNA Library Production:

cDNA libraries were constructed with the SMART cDNA library construction kit (Clontech laboratories) according to the manufacturer's instructions. The cDNA was size selected with a molecular weight cutoff of 500 base pairs by agarose gel electrophoresis. The plasmid vector pMHas7 (SEQ ID NO: 3) was used instead of the phage vector supplied with the kit. Plasmid DNA was isolate from a pool of 50,000 colonies, scraped from LB kanamycin selection plates (kanamycin 50 mg/l). Plasmid from the pooled bacteria was used for preparation of plasmid library using the JetStar midi plasmid purification method (Genomed.com).

Identification of a Tyrosinase Encoding cDNA from Sequencing of Selected Plasmids of the cDNA Library:

A complete description of transposon assisted signal trapping can be found in WO 01/77315. A cDNA plasmid pool was prepared from 30,000 total transformants of the original cDNA-pMHas7 vector ligation. Plasmid DNA was prepared directly from a pool of colonies recovered from solid LB selective media according to the Qiagen Midiprep protocol for plasmid DNA isolation (QIAGEN, Inc., Valencia, Calif., USA). The plasmid pool was treated with transposon SigA2 and MuA transposase (Finnzymes OY, Espoo, Finland) according to the manufacturer's instructions.

For in vitro transposon tagging of the cDNA library, 4 or 8 ul of SigA2 transposon containing approximately 2.6 ug of DNA was mixed with 3 ul of the plasmid DNA pool of the cDNA library containing 320 ng/ul of DNA, 2 ul of MuA transposase (0.22 ug/ul), and 5 ul of 5× buffer (Finnzymes OY, Espoo, Finland) in a total volume of 50 ul and incubated at 30° C. for 3.5 hours followed by heat inactivation at 75° C. for 10 minutes. The DNA was precipitated by addition of 5 ul of 3 M sodium acetate pH 5 and 110 ul of 96% ethanol and centrifuged for 30 minutes at 10,000×g. The pellet was washed in 70% ethanol and air dried at room temperature before resuspension in 10 ul of 10 mM Tris, pH 8, 1 mM EDTA (TE) buffer.

A 1.5 ul volume of the transposon tagged plasmid pool was electroporated into 20 ul of *E. coli* DH10B ultracompetent cells (Gibco-BRL, Gaithersburg Md., USA) according to the manufacturer's instructions using a GENE PULSER® and Pulse Controller (Bio-Rad, Hercules, Calif., USA) at 50 uF, 25 mAmp, 1.8 kV with a 2 mm gap cuvette according to the manufacturer's procedure.

The electroporated cells were incubated in SOC medium with shaking at 250 rpm for 2 hours at 28° C. before being plated on the following selective media: LB medium supplemented with 50 ug of kanamycin per ml; LB medium supplemented with 50 ug of kanamycin per ml and 15 ug of chloramphencol per ml; and/or LB medium supplemented with 50 ug of kanamycin per ml, 15 ug of chloramphencol per ml, and 12.5 ug of ampicillin per ml.

From dilution plating of the electroporation onto LB medium supplemented with kanamycin and chloramphencol medium, it was determined that approximately 72,000 colonies were present containing a cDNA library plasmid with a SigA2 transposition per electroporation and that approximately 69 colonies were recovered under triple selection (LB, kanamycin, chorlamphenicol, ampicillin). Further electroporation and plating experiments were performed until 445 total colonies were recovered under triple selection. The colonies were miniprepped according to the QIAprep 96 Turbo Miniprep Kit (QIAGEN Inc., Valencia, Calif., USA). Plasmids were sequenced with the transposon forward and reverse primers (primers A and B), shown below, according to the procedure disclosed in WO 01/77315 (page 28):

```
Primer A:
5'-AGCGTTTGCGGCCGCGATCC-3'      (SEQ ID NO: 4)

Primer B:
5'-TTATTCGGTCGAAAAGGATC C-3'    (SEQ ID NO: 5)
```

Sequence Assembly and Annotation:

DNA sequences were obtained for the reactions on an ABI PRISM Automated DNA Sequencer Model 3700 (Applied Biosystems, Foster City, Calif., USA). Primer A and primer B sequence reads for each plasmid were trimmed to remove vector and transposon sequence. This resulted in 225 assembled sequences which were grouped into 170 contigs by using the program PhredPhrap (Ewing et al., 1998, Genome Research 8: 175-185; Ewing and Green, 1998, Genome Research 8: 186-194). All 170 contigs were subsequently compared to sequences available in standard public DNA and protein sequences databases (TrEMBL, SWALL, PDB, EnsemblPep, GeneSeqP) by using the program BLASTX 2.0a19MP-WashU [14-Jul-1998] [Build linux-x86 18:51:44 30-Jul-1998] (Gish et al., 1993, Nat. Genet. 3: 266-72).

The tyrosinase candidate was identified directly by analysis of the BlastX results from the project above.

Expression of Tyrosinase from *Botryosphaeria obtusa*:

*Bottyosphaeria obtusa* is available from the Centraalbureau voor Schimmelcultures (CBS719.85).

The cDNA library of *Botryosphaeria obtusa* was made according to above method. Mycelia of *Botryosphaeria obtusa* was cultured on wheat bran+YNB.

YNB media:
1.8 g Yeast Nitrogen Base
5 g Ammonium sulfate
1000 ml water

The culture was incubated stationary at 26° C. for 7 days. Mycelia was harvested and frozen in liquid nitrogen then stored at −80° C. until use. The sequence identified in the previous section was used to design two PCR primers that were used for producing a DNA expression cassette suitable for cloning into the *Aspergillus oryzae* expression plasmid pXYG1051 (WO 2005/080559).

The following primers were used (Restriction sites introduced for cloning purposes are underlined):

```
NP1127RI:
                              (SEQ ID NO: 6)
5'-GCGGAATTCACCATGCGTCTTTTCGACATCTC-3'

NP1127NotI:
                              (SEQ ID NO: 7)
5'-ATTTGCGGCCGCAAACAAGCCCATGATACACGAACAG-3'
```

1 microliter of *Bottyosphaeria obtusa* plasmid cDNA library (approximately 10 nanograms of DNA) was used as template in a PCR reaction with the two primers NP1127RI and NP1127NotI.

5 pmol of each primer was used in a 50 microliter reaction volume. The Qiagen ProofStart high fidelity DNA polymerase and buffer were used according to the manufacturer's instructions (Qiagen, USA). Briefly, the reaction was placed in a thermal cycler (MJ Research, Dyad, USA) and cycled under the following reaction conditions: An initial denaturation of 5 minutes at 95 degrees Celsius, 25 cycles of the following: 94 degrees for 30 seconds, 55 degrees for 30 seconds, 72 degrees for 2 minutes. A final extension temperature of 72 degrees for 10 minutes was then used. Aliquots of the PCR reaction were separated on a 1% agarose gel. One band was seen: The size of this band appeared with the expected size of 1634 bp.

The fragment was digested with EcoRI and NotI which cut in the overhangs introduced by the PCR primers. A standard ligation into pXYG1051 and transformation into *E. coli* Top10 cells (Invitrogen) resulted in several plasmids being identified. Plasmid DNA was isolated from colonies of the cloning experiment. The colonies were sequenced with vector primers PNA2 (5'-GTT TCC AAC TCA ATT TAC CTC-3' (SEQ ID NO: 8)) and TAMG (5'-TTG CCC TCA TCC CCA TCC TTT-3' (SEQ ID NO: 9)) which prime in opposite directions into the plasmid insert. A single plasmid was chosen for transformation into *Aspergillus oryzae*.

The *Aspergillus* transformation plasmid NP001127-5 containing SEQ ID NO: 1 was transformed into *Aspergillus oryzae* strain JAL355 (disclosed in international patent application WO 01/98484A1). Transformants of NP001127-5 were re-isolated twice under selective and non-inducing conditions on Cove minimal plates (Cove (1966) Biochim. Biophys. Acta 133:51-56) with 1M sucrose as a carbon source and 10 mM nitrate. To test expression of SEQ ID NO: 1, transformants were grown for 3 days and 4 days at 30 degrees Celsius in tubes with 10 ml YPG (2% peptone, 1% yeast extract, 2% glucose). Supernatants were run on NuPage® 10% Bis-Tris SDS gels (Invitrogen, USA) as recommended by the manufacturer. All *Aspergillus* isolates grew well on YPG media when induced for the expression of the DNA of SEQ ID NO: 1. One single transformant judged to make sufficient quantities of the tyrosinase was named EXP00856 and was chosen for further fermentation.

Two liters of EXP00856 was fermented in YPM media and the culture fluid was separated from the biomass by miracloth filtration. The tyrosinase was purified from the culture fluid and frozen until further use.

Example 2

Characterization of Tyrosinase from *Botryosphaeria obtusa* pH Profile 20 ul diluted samples of the tyrosinase from Example 1 (diluted in 20 mM sodium phosphate pH 6.5) were added to a micro titre plate (A280 transparent) and 200 ul 1 mM tyrosine, 100 mM succinic acid, 100 mM HEPES, 100 mM CHES, 1 mM $CuCl_2$ (various pH, 3-9) were added and incubated for 15 min at 25° C. The reaction was stopped with 20 ul 4M HCl and the absorbance at 280 nm was measured.

TABLE 2.1

| pH | relative activity (pH 6 = 100%) |
|---|---|
| 3 | −1 |
| 4 | 4 |
| 5 | 45 |
| 6 | 100 |
| 7 | 80 |
| 8 | 17 |
| 9 | −3 |

Temperature Profile 200 ul 50 mM MES pH 6.5, 1 mM tyrosine, 1 mM $CuCl_2$ were added to Eppendorf tubes and incubated for 5 min (preheating). Hereafter 20 ul diluted enzyme was added and incubated for 15 min at various temperatures (37-80° C.). The reaction was stopped by adding 20 ul 200 mM sodium-EDTA followed by incubation at 95° C. for 2 min. The solution was transferred to a micro titre plate and absorption at A480 was measured.

TABLE 2.2

| Temp (° C.) | Relative activity (50° C. = 100%) |
|---|---|
| 37 | 86 |
| 50 | 100 |
| 60 | 99 |
| 70 | 55 |
| 80 | 4 |

Example 3

Activation of Tyrosinase from *Botryosphaeria obtusa*

Activation of tyrosinase from *Botryosphaeria obtusa* with protease from *Bacillus licheniformis* was made with various protease concentrations and hereafter the MW change and tyrosinase activity was measured. As seen below, the increase in tyrosinase activity correlates to the intensity of the "45 kDa" band. Thus, the full length 60 kDa form is a low-active pro form which can be activated to amore active "45 kDa" form.

Activation of Tyrosinase 100 ul 30 ug/ml tyrosinase in 50 mM succinic acid, 50 mM HEPES, 50 mM CHES, 0.1 mM $CuCl_2$ pH 6.5, 0.01% Triton ×100, was placed in a micro titre plate and 10 ul diluted *Bacillus licheniformis* protease solution in 50 mM succinic acid, 50 mM HEPES, 50 mM CHES, 0.1 mM $CuCl_2$ pH 6.5, 0,01% Triton ×100 (various protease concentrations were used, see Table 3.1, final concentrations) was added and incubated for 30 min. The proteolytic activity was stopped with 5 ul 0.1 M PMSF.

Activity Assay

Activated tyrosinase, 20 ul, was added to a micro titre plate followed by the addition of 200 ul 2 mg/ml sodium caseinate in 50 mM succinic acid, 50 mM HEPES, 50 mM CHES, 0.1 mM $CuCl_2$ pH 6.5. This solution was incubated 30 min. at room temp. (24° C.) and the absorbance at 480 nm was recorded in a micro titre plate reader.

MW Change Analysis Using SDS-PAGE 25 ul activated tyrosinase and 25 ul sample buffer (22.5 uL Novex LC2676 Tris-Glycine SDS sample buffer+2.5 ul 1 M DTT) was mixed and incubated for 5 min at 95° C. 20 ul of this solution was added on a Nu-PAGE 4-12% Bis-Tris gel. The gel was stained with Coomassie Blue (SimplyBlue LC6065 Invitrogen). Two forms of the tyrosinase was seen on the SDS gel as bands of appr. 60 and 45 kDa. At 0 ug/ml protease, the 60 kDa band was clear and distinct and the 45 kDa form was barely traceable. At 11 and 33 ug/ml protease, the 60 kDa form was not visible, whereas the 45 kDa band was as clear and distinct as the 60 kDa band at 0 ug/ml. The relative intensity of the two bands in each lane was estimated by visual inspection of the gel and given in Table 3.1 below.

TABLE 3.1

| Protease ug/ml | Relative activity increase % of no protease added | 60 kDa band Relative intensity | 45 kDa band Relative intensity |
|---|---|---|---|
| 33 | 1082 | − | +++ |
| 11 | 886 | − | +++ |
| 4 | 814 | + | ++ |
| 1.2 | 655 | ++ | ++ |
| 0.4 | 308 | ++ | + |
| 0.1 | 192 | ++ | + |
| 0.04 | 172 | +++ | + |
| 0 | 100 | +++ | − |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide which has an amino acid sequence at least 95% identical to the sequence of SEQ ID NO: 2, and wherein the polypeptide has tyrosinase activity.

2. The polypeptide of claim 1, having an amino acid sequence at least 97% identical to the sequence of SEQ ID NO: 2.

3. The polypeptide of claim 1, which comprises the amino acid sequence of SEQ ID NO: 2.

4. The polypeptide of claim 1, which consists of the amino acid sequence of SEQ ID NO: 2.

5. The polypeptide of claim 1, which comprises the amino acid sequence of the mature protease from position 34 to position 392 of SEQ ID NO: 2.

6. The polypeptide of claim 1, which consists of the amino acid sequence of the mature protease from position 34 to position 392 of SEQ ID NO: 2.

7. A method of modifying a protein-containing material, wherein said material is contacted with a polypeptide which has an amino acid sequence at least 95% identical to the sequence of SEQ ID NO: 2, and wherein the polypeptide has tyrosinase activity.

8. The method of claim 7, wherein the protein-containing material is a food material.

9. A composition comprising the isolated polypeptide of claim 1.

10. The composition of claim 9, wherein the polypeptide has an amino acid sequence at least 97% identical to the sequence of SEQ ID NO: 2.

11. The composition of claim 9, wherein the polypeptide comprises the amino acid sequence of SEQ ID NO: 2.

12. The composition of claim 9, wherein the polypeptide consists of the amino acid sequence of SEQ ID NO: 2.

13. The composition of claim 9, wherein the polypeptide comprises the amino acid sequence of the mature protease from position 34 to position 392 of SEQ ID NO: 2.

14. The composition of claim 9, wherein the polypeptide consists of the amino acid sequence of the mature protease from position 34 to position 392 of SEQ ID NO: 2.

15. The composition of claim 9, which is in the form of a liquid.

16. The composition of claim 9, which is in the form of a dry composition.

17. The composition of claim 9, further comprising additional enzymatic activities.

* * * * *